US012691145B2

(12) United States Patent
Canal Barnils et al.

(10) Patent No.: US 12,691,145 B2
(45) Date of Patent: Jul. 28, 2026

(54) PLASMA-TREATED HYDROGEL COMPOSITIONS AND USES THEREOF

(71) Applicant: UNIVERSITAT POLITÉCNICA DE CATALUNYA, Barcelona (ES)

(72) Inventors: Cristina Canal Barnils, Barcelona (ES); Cédric Labay, Barcelona (ES); Xavi Solé Martí, Barcelona (ES); Maria-Pau Ginebra Molins, Barcelona (ES)

(73) Assignee: UNIVERSITAT POLITÉCNICA DE CATALUNYA, Barcelona (ES)

( * ) Notice: Subject to any disclaimer, the term of this patent is extended or adjusted under 35 U.S.C. 154(b) by 627 days.

(21) Appl. No.: 18/247,821

(22) PCT Filed: Jun. 17, 2021

(86) PCT No.: PCT/EP2021/066437
§ 371 (c)(1),
(2) Date: Apr. 4, 2023

(87) PCT Pub. No.: WO2021/255179
PCT Pub. Date: Dec. 23, 2021

(65) Prior Publication Data
US 2023/0372391 A1 Nov. 23, 2023

(30) Foreign Application Priority Data

Jun. 18, 2020 (EP) .................................... 20382527

(51) Int. Cl.
| | |
|---|---|
| *A61K 33/40* | (2006.01) |
| *A61K 33/00* | (2006.01) |
| *A61K 47/02* | (2006.01) |
| *A61K 47/36* | (2006.01) |
| *A61K 47/42* | (2017.01) |
| *A61L 27/12* | (2006.01) |
| *A61L 27/26* | (2006.01) |
| *A61L 27/54* | (2006.01) |
| *A61P 35/00* | (2006.01) |

(52) U.S. Cl.
CPC .............. *A61K 33/40* (2013.01); *A61K 33/00* (2013.01); *A61K 47/02* (2013.01); *A61K 47/36* (2013.01); *A61K 47/42* (2013.01); *A61L 27/12* (2013.01); *A61L 27/26* (2013.01); *A61L 27/54* (2013.01); *A61P 35/00* (2018.01); *A61L 2300/11* (2013.01); *A61L 2300/114* (2013.01); *A61L 2300/40* (2013.01); *A61L 2400/12* (2013.01); *A61L 2430/02* (2013.01)

(58) Field of Classification Search
CPC ........ A61K 33/40; A61K 33/00; A61K 47/02; A61K 47/36; A61K 47/42; A61P 35/00; A61L 27/12; A61L 27/26; A61L 27/54; A61L 2300/11; A61L 2300/114; A61L 2300/40; A61L 2400/12; A61L 2430/02
See application file for complete search history.

(56) References Cited

U.S. PATENT DOCUMENTS

2019/0274747 A1 9/2019 Chen et al.

FOREIGN PATENT DOCUMENTS

| | | | | | |
|---|---|---|---|---|---|
| CN | 110354005 A | * | 10/2019 | ............. | A61K 8/042 |
| CZ | 33289 U1 | * | 10/2019 | ............... | H01G 9/20 |
| WO | 2010146438 A1 | | 12/2010 | | |
| WO | WO-2015123720 A1 | * | 8/2015 | ............. | A61L 2/0011 |
| WO | WO-2017161153 A1 | * | 9/2017 | ............. | A61B 18/02 |

OTHER PUBLICATIONS

Machine translation of CN-110354005-A (Year: 2019).*
Liebmann et al.; Biological effects of nitric oxide generated by an atmospheric pressure gas-plasma on human skin cells; Elsevier; Nitric Oxide 24 (2011) 8-16 (Year: 2011).*
Wang et al.; Design of Biomimetic and Bioactive Cold Plasma-Modified Nanostructured Scaffolds for Enhanced Osteogenic Differentiation of Bone Marrow-Derived Mesenchymal Stem Cells; Mary Ann Liebert, Inc.; Tissue Engineering: Part A, vol. 20, No. 5 and 6, 1060-1071 (Year: 2014).*
Machine translation of CZ-33289-U1 (Year: 2019).*
Canal Barnils et al., "Modification of drug release from doxorubicin-loaded calcium phosphate microspheres by plasma polymerization", Feb. 13, 2020, https://upcommons.upc.edu/handle/2117/182178?show=full.
Labay et al., "Production of reactive species in alginate hydrogels for cold atmospheric plasma-based therapies", Scientific Reports, 2019, vol. 9, No. 1.
Liu et al., "Preparation of porous calcium phosphate microspheres with phosphate-containing molecules at room temperature for drug delivery and osteogenic differentiation", RSC Adv., 2018, pp. 25480-25488, vol. 8, No. 45.
Wang et al., "Design of Biomimetic and Bioactive Cold Plasma-Modified Nanostructured Scaffolds for Enhanced Osteogenic Differentiation of Bone Marrow-Derived Mesenchymal Stem Cells", Tissue Engineering: Part A, 2014, pp. 1060-1071, vol. 20, Nos. 5 and 6.

* cited by examiner

*Primary Examiner* — Robert A Wax
*Assistant Examiner* — John W Lippert, III
(74) *Attorney, Agent, or Firm* — The Webb Law Firm

(57) ABSTRACT

The present invention relates to a composition including a polymer aqueous solution, a bioceramic material and reactive oxygen and nitrogen species (RONS) and its use for the treatment of bone cancer and/or bone tissue regeneration.

17 Claims, 3 Drawing Sheets

100 μm

A

300 μm

B

300 μm

A

B

PLASMA-TREATED HYDROGEL COMPOSITIONS AND USES THEREOF

CROSS-REFERENCE TO RELATED APPLICATIONS

This application is the United States national phase of International Application No. PCT/EP2021/066437 filed Jun. 17, 2021, and claims priority to European Patent Application No. 20382527.8 filed Jun. 18, 2020, the disclosures of which are hereby incorporated by reference in their entireties.

BACKGROUND OF THE INVENTION

Field of the Invention

The present invention belongs to the field of Biotechnology and relates to a composition comprising a polymer aqueous solution, a bioceramic material and reactive oxygen and nitrogen species (RONS) and its use for the treatment of bone cancer or bone tissue regeneration.

Description of Related Art

In the last years, great advances have been made in therapies based in cold atmospheric plasmas (CAP). CAP generate reactive oxygen and nitrogen species (RONS) which can be transferred to liquids. These CAP activated liquids display similar biological efficacy (i.e. on killing cancer cells) as CAP themselves, opening the door for minimally invasive therapies. However, injection of a liquid in the body results in fast diffusion due to extracellular fluids and blood flow. Therefore, the development of efficient vehicles which allow local confinement and delivery of RONS to the diseased site is a fundamental requirement.

Plasma is defined as a totally or partially ionized gas that contains a high number of reactive species, ions, electrons, metastable particles, etc. The development of plasma sources of small dimensions and able to operate at atmospheric pressure and at temperatures close to room temperature has fostered the development of a new field named Plasma medicine. Atmospheric pressure plasma (APP) has been evaluated as an effective tool for sterilization, cancer treatment or for enhancing wound healing. APPs formed in air generate reactive oxygen and nitrogen species (RONS), which can be transferred to liquids through secondary reactions. Plasma-activated liquids (PAL) display different biological actions which have been mainly attributed to the generation of RONS such as hydrogen peroxides ($H_2O_2$), nitrites ($NO_2^-$), peroxynitrites, etc. These reactive species are known to be involved in a wide range of intracellular and intercellular processes. Until now, major attention has been paid in plasma medicine to the monitoring of RONS induced in PAL used in indirect treatments, and some works have investigated their storage by freezing the PAL but this is not always possible. However, transportation and diffusion from suitable biomaterials of these RONS for in situ therapy remains to be explored. Labay et al. Scientific Reports 9:16160 (2019) relates to alginate-based hydrogels as vehicles of RONS generated by atmospheric plasmas and studies whether there are any chemical modifications in the structure of the alginate and its hydrogel-forming ability. The biocompatibility of the plasma-treated polymer and cytotoxicity of the RONS generated therein is also investigated.

WO15123720 A1 relates to a plasma treatment method comprising: providing a plasma source and a screen comprising a hydrogel and positioning the screen between the plasma source and a surface of a target to be treated; and/or contacting a surface of a target to be treated with the gel composition comprising a gel forming material and a liquid phase comprising plasma activated liquid.

WO10146438 A1 relates to the use of collagen or chitosan solutions treated with plasma for wound healing.

US2019274747 relates to the use of cold atmospheric plasma generated RONS for treating cancer, particularly pancreatic and breast cancer.

There is a need for improved compositions to be used in the treatment of cancer, which are both biocompatible and effective.

SUMMARY OF THE INVENTION

The present invention provides compositions useful for the treatment of cancer. Surprisingly, the inventors have found that compositions comprising a polymer solution, a bioceramic material comprising calcium and RONS in certain concentrations are useful in killing cancer cells while do not alter the viability of healthy cells. These compositions can be injected or implanted in the body, where they release the RONS to the surrounding medium and kill specifically cancer cells.

Thus, in a first aspect, the present invention relates to a composition comprising a polymer aqueous solution, a bioceramic material comprising calcium, and reactive oxygen and nitrogen species (RONS), wherein said RONS comprise between 0.68 and 200.00 mg/L $H_2O_2$ and/or between 0.46 and 36.80 mg/L $NO_2^-$.

As used herein, polymer aqueous solution is a water-based solution of a polymeric substance. When said polymer solution polymerizes and/or crosslinks, a hydrogel is formed. The polymer solution can also be referred to as hydrosol, before polymerization or crosslinking.

As used herein, a bioceramic material is any biologically compatible ceramic material.

As used herein, the term reactive oxygen and nitrogen species or RONS, refers to $H_2O_2$, $OH^*$, $NO_2^-$, $NO_3^-$, $ONOO^-$. In the present invention, the RONS in the composition are generated by means of treating either the polymer aqueous solution or the polymer aqueous solution and the calcium-comprising bioceramic material, with cold atmospheric plasma. The skilled person knows how to treat a liquid with cold atmospheric plasma in order to obtain the desired RONS concentrations, and extensive details are given in the examples.

In a preferred embodiment of the present invention, the RONS in the composition comprise between 12.00 and 150.00 mg/L $H_2O_2$, preferably between 13.60 and 150.00 mg/L $H_2O_2$. In a preferred embodiment, the RONS in the composition comprise between 13.80 and 36.80 mg/L $NO_2$, more preferably between 18.40 and 36.80 mg/L $NO_2$.

In a preferred embodiment, the RONS in the composition comprise between 5.10 and 200.00 mg/L $H_2O_2$ and between 0.46 and 36.80 mg/L $NO_2$. In another preferred embodiment, the RONS in the composition comprise between 0.68 and 150.00 mg/L $H_2O_2$ or between 1.90 and 200.00 mg/L $H_2O_2$ or between 3.00 and 200.00 mg/L $H_2O_2$. In a preferred embodiment, the RONS in the composition comprise between 15.30 and 200.00 mg/L $H_2O_2$. In another preferred embodiment, the RONS in the composition comprise between 51.00 and 200.00 mg/L $H_2O_2$.

The RONS concentration is quantified either using the AR/HRP reagent method or the Griess reagent method for $H_2O_2$ and $NO_2^-$, respectively, or using plastic strips with test paper which allow quantification of $H_2O_2$ based or a redox reaction and $NO_2^-$, also using the Griess reagent. These two methods give equivalent results, as shown in the experimental section. Therefore, the skilled person knows which method to use for each polymer solution in the composition, since protein solutions may cause interferences with the AR/HRP reagent method or the Griess reagent method, which are solved when using the strips.

In a preferred embodiment of the composition of the first aspect, the polymer is selected from gelatin and its derivatives, such as methacrylated gelatin, fibrin, fibronectin, collagen, and collagen derivatives, alginate, agarose, cellulose, modified cellulose, such as hydroxypropyl cellulose, methylcellulose, carboxymethylcellulose or hydroxyethyl cellulose, xantan gum, polyethylene glycol, hyaluronic acid, chitosan, polylactide-co-glycolide, polyhydroxyalcanoates and mixtures thereof, preferably is selected from gelatin and its derivatives, alginate, collagen and mixtures thereof.

In a preferred embodiment of the composition of the first aspect, the composition comprises between 0.15 and 50.00 weight % of polymer in respect of the total weight of the composition, preferably between 0.50 and 20.00 weight % of polymer in respect of the total weight of the composition, more preferably between 1.00 and 10.00% of polymer in respect of the total weight of the composition. In particular embodiments, the composition comprises between 1.00 and 5.00 weight % of polymer in respect of the total weight of the composition.

In a preferred embodiment of the composition of the first aspect, the bioceramic material comprising calcium comprises calcium phosphate. In a preferred embodiment, the bioceramic material comprising calcium is other than calcium carbonate. Preferably, the bioceramic material comprising calcium is selected from tetra-calcium phosphate, dicalcium phosphate anhydrous, dicalcium phosphate dihydrate, alpha-tricalcium phosphate, beta-tricalcium phosphate, monocalcium phosphate monohydrate, hydroxyapatite, calcium deficient hydroxyapatite, fluorapatite, amorphous calcium phosphate, calcium-sodium and potassium-phosphate, calcium- and sodium-phosphate, calcium- and potassium-phosphate, calcium pyrophosphate, calcium carbonate, calcium sulphate, calcium sulphate hemihydrate, calcium oxide and calcium hydroxide, and mixtures thereof.

In a preferred embodiment of the composition of the first aspect, the bioceramic material is hydroxyapatite, brushite, tricalcium phosphate or mixtures thereof.

In a preferred embodiment of the composition of the first aspect, the bioceramic material is in form of nanoparticles, microspheres, microparticles, foams or scaffold, or mixtures thereof. When the bioceramic material is in form of nanoparticles, microspheres or microparticles, the composition can be injected. In said cases, the compositions are suitable for forming implant upon injection in the body. When the bioceramic material is in form of foams or scaffolds, the composition is suitable for being implanted in the body. Therefore, the compositions of the invention can be used for the treatment of a cancer in a subject in need thereof by either injecting or implanting the composition in the body of the subject, so that the RONS released from the composition kill the cancer cells while not damaging the healthy tissue.

In a preferred embodiment of the composition of the first aspect, the composition comprises between 0.5 and 99.5 weight % of bioceramic materials in respect of the total weight of the composition. When the bioceramic material is in form of nanoparticles, microspheres or microparticles, the compositions preferably comprise between 0.5 and 20.0 weight % of bioceramic materials in respect of the total weight of the composition, more preferably between 0.5 and 10.0 weight % of bioceramic materials in respect of the total weight of the composition. When the bioceramic material is in form of foams or scaffolds, the compositions preferably comprise between 20.0 and 99.5 weight % of bioceramic materials in respect of the total weight of the composition, more preferably between 50.0 and 85.0 weight % of bioceramic materials in respect of the total weight of the composition.

In a preferred embodiment of the composition of the first aspect, the pH of the composition is between 5.0 and 8.0, preferably between 6.0 and 7.5, measured according to ASTM E70.

In a preferred embodiment of the composition of the first aspect, the composition further comprises an active pharmaceutical ingredient. Preferably, the active pharmaceutical ingredient is a chemotherapeutic drug or a coadjuvant in the cancer therapy. The drug can also be an antibiotic to prevent infection. Different kinds of drugs can be incorporated/loaded to the bioceramic component of the composition or in the hydrogel component. These can include chemotherapeutic drugs (i.e. methotrexate, cisplatin, doxorubicin, ifosfamide, etoposide, bleomycin) or other therapeutics, such as monoclonal antibodies, cytokines, and specific inhibitors of different proteins related with disease progression, or other biomolecules. In a preferred embodiment, the drug or drugs is/are contained in the bioceramic component of the composition. The drugs, either in free form or encapsulated (liposomes, etc.) can remain entrapped in the bioceramic material, in the hydrogel or in both, and can be released to the surrounding media.

The composition of the first aspect of the invention can be frozen (for example, using liquid nitrogen) after mixing the plasma treated hydrogel and the bioceramic material. Preferably, right after the plasma treatment of the hydrogel, said hydrogel is mixed with the bioceramic material and the composition is frozen using liquid nitrogen.

A second aspect of the present invention relates to the composition of the first aspect for use in the treatment of cancer. Preferably, the cancer is bone cancer, more preferably, osteosarcoma. As used herein, the term bone cancer refers to chondrosarcoma, Ewing's sarcoma, osteosarcoma or metastatic bone cancer.

A third aspect of the present invention relates to the composition of the first aspect for use in bone tissue regeneration. The inventors have found that the compositions of the invention, in addition to being useful in selectively killing cancer cells, are also useful in promoting bone tissue regeneration, due to their biocompatibility and thanks to the bioceramic component.

A fourth aspect of the present invention is a process for preparing the compositions of the first aspect, which comprises the following steps: (a) preparing a polymer aqueous solution, (b) adding a bioceramic material comprising calcium, (c) treating either the solution of step (a) or the solution with the calcium comprising bioceramic material of step (b) with cold atmospheric plasma so that the solution comprises between 0.68 and 102.00 mg/L $H_2O_2$ and/or between 0.46 and 36.80 mg/L $NO_2^-$.

EXAMPLES

Figure 1:
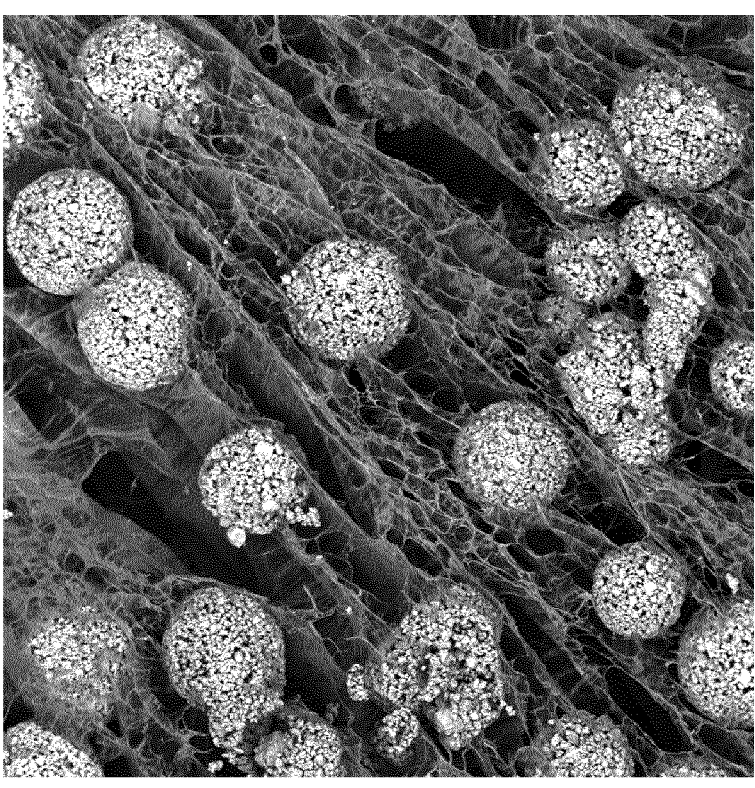
FIG. 1: SEM image of the composition of Example 6 after freeze-drying.

The following examples are provided to further illustrate, but not to limit this invention.

Materials

Gelatin type B (Rousselot 250 LB8, Rousselot, France), sodium alginate (MW: 10000-600000 g/mol) (Panreac, USA), both in powder form, and MilliQ water (MilliPore, Merck) were used for preparation of polymer solutions. Argon (Ar 5.0, PRAXAIR, Spain) was employed as precursor gas for APP generation in polymer solutions.

Sulphanilamide (Sigma Aldrich, USA), N-(1-naphthyl) ethylenediamine dihydrochloride (Sigma Aldrich, USA) and Ortho-Phosphoric Acid 85%, pure, pharma grade (USP-NF, BP, Ph. Eur.) ($H_3PO_4$) (85%) (Panreac, USA) have been used for the preparation of Griess reagent, used for $NO_2^-$ detection. $NaNO_2$ (Sodium nitrite, Sigma Aldrich, USA) was used for calibration curves of nitrites. Amplex™Red reagent (Invitrogen™, Thermo Fisher Scientific) and Peroxidase from Horseradish (Type VI) (HRP) (Sigma Aldrich) were used for determination of $H_2O_2$ in liquid solutions. 30% (w/w) $H_2O_2$ solution (Sigma Aldrich) was used for calibration curve for $H_2O_2$ detection in MilliQ water.

Sarcoma osteogenic cells (SaOs-2, ATCC, USA) were expanded in McCoy's 5A culture medium (Sigma Aldrich). Foetal Bovine Serum (FBS) and Penicillin/Streptomycin (P/S) (50 U/ml and 50 μg/ml, respectively) were purchased from Invitrogen. Bone marrow-derived Mesenchymal Stem Cells (hMSC, PCS-500-012, #70014245, ATCC, USA) were cultured in Advanced Dulbecco's Eagle Medium (1×) (AdvDMEM) (Gibco, ThermoFisher Scientific). Cells from passage between 24 and 32 were used in all experiments. Cell Proliferation Reagent WST-1 (Roche Diagnostics GmbH, ref. 05015944001) and PrestoBlue™ Cell Viability Reagent (Invitrogen™, Thermo Fisher Scientific, ref. A13261) were used for cell viability determination.

Methods

Preparation of Polymeric Solutions.

Different polymeric solutions were prepared by dissolving in water or aqueous saline solutions suitable concentrations polymers such as fibrin, fibronectin, collagen, alginate, gelatin, etc, and mixtures thereof. As an example, a detailed description of the procedure followed for the preparation of alginate and gelatin solutions is included below:

Alginate solutions were obtained by mixing the dry sodium-alginate powder with DI water in a SpeedMixer (DAC 150.1 FVZ-k, 3500 rpm) for 15 min at 0.5% w/w. The solutions can also be obtained by stirring with a conventional stirrer for longer times.

For the preparation of gelatin solutions, gelatin in powder was mixed with MilliQ water at 37° C. using magnetic stirring for 2 hours to obtain a 2% wt gelatin solution. Gelatin solutions were stored at 4° C. and used within a lifespan of 2 weeks. Both gelatin and alginate powder solutions were filtered at 37° C. using a 0.22 μm syringe filter before cell experiments (Millipore, Merck). For cell experiments, all the processes leading to the preparation of the formed polymer solution or hydrogel were carried out under sterile conditions.

Plasma Treatments.

In the examples presented here, two kinds of atmospheric plasma jet were used: a commercially available cold atmospheric plasma jet kINPen IND (NEOPLAS Tools, Germany), operating with argon and an atmospheric pressure plasma jet (APPJ) using He as plasma gas in a jet design based on a single electrode. Gas flow was regulated between 1 and 2.5 L/min for kINPen and between 1 and 5 L/min for APPJ by using Ar and He Bronkhorst Mass View flow controllers (BRONKHORST, Netherlands), respectively. All plasma treatments of polymeric solutions for RONS quantification were performed on 200 μL of the polymeric solution in 96-well plates, with a distance between the nozzle and the sample surface between 10 and 20 mm. These plasma treatments were done with ungrounded samples. Both grounded and ungrounded samples can be used to obtain the compositions of the present invention, since the skilled person can set the plasma treatment conditions to obtain the desired RONS concentrations.

Preparation of the Compositions

To prepare the compositions of the present invention, the plasma-treated polymeric solutions were blended with the calcium containing biomaterial. The method for blending and preparing the compositions may vary depending on the actual morphology/shape of the calcium comprising material. In the case of calcium phosphate nanoparticles, mixing with the polymer solution can be done manually, in a double-syringe system, using a SpeedMixer or any other method ensuring homogeneous dispersion. In this case, the mixture can be done with polymer solution containing RONS or alternatively treat the composition with plasma to transfer the RONS to the composition after mixing of the polymer solution and the calcium phosphate phase. If the plasma treatment is applied to the composition comprising the polymer solution and the calcium comprising material, then the treatment has to be applied before polymerization or crosslinking (gelation) of the polymer.

In the case of bioceramics in the shape of scaffolds, mixing should be done with the RONS— containing polymer solution, and different methods may be considered, namely by immersion, employing two syringes, dropwise addition, etc.

Detection of RONS in the Polymer Solutions.

Determination of $NO_2^-$ concentration in plasma-treated polymer solutions was performed using Griess reagent. The Griess reagent used was obtained by dissolving 1% wt/v of sulphanilamide, 0.1% wt/v of N-(1-naphthyl)ethylenediamine dihydrochloride (NEED) and 5% w/v of phosphoric acid in de-ionized water. 200 μL of Griess reagent were added on 200 μL of sample in 96 well-plates. The plates were incubated for 10 min at room temperature protected from the light. The absorbance was measured at $\lambda_{abs}$=540 nm using a Synergy HTX Hybrid Multi Mode Microplate Reader (BioTek Instruments, Inc., USA). The $[NO_2^-]$ in each sample was determined from the absorbance values by using a calibration curve made from $NaNO_2$ dilutions in the corresponding polymer solutions.

The concentration of hydrogen peroxide was determined by reaction of $H_2O_2$ with Amplex Red in presence of HRP enzyme that leads to the creation of resorufin, a fluorescent product. Amplex Red/HRP reagent consists in 100 µM of Amplex Red and 0.25 U/mL HRP in DI water. Since the higher concentration of $H_2O_2$ able to be processed properly by this reagent is around 10 µM of $H_2O_2$, plasma-treated polymer solutions were diluted 200 times previously to the addition of the reagent. In this case, for hydrogen peroxide detection, 50 µL of the Amplex Red/HRP reagent was added to 200 µL of the 200×-diluted polymer solution sample in a 96-well plate and incubated for 30 min at 37° C. Subsequent fluorescence measurements were performed by means of a Synergy HTX Hybrid Multi Mode Microplate Reader (BioTek Instruments, Inc., USA), with fluorescence filters centred at $\lambda_{ex}$=560/20 nm and $\lambda_{em}$=590/20 nm as excitation and emission wavelengths, respectively. Concentrations of $H_2O_2$ in polymer solution generated by plasma treatment were obtained from the fluorescence values using a calibration curve made from 30% hydrogen peroxide solution in the corresponding polymer solutions.

Also, the chemical probe coumarin (Sigma Aldrich, USA) was employed to detect hydroxyl radicals (OH). Different polymer solutions were prepared in 1 mM coumarin, and different plasma-treatment times were evaluated. In solution, OH radicals react with coumarin giving a fluorescent product: 7-hydroxycoumarin (7-hC). The fluorescence intensity of 500 µL of plasma-treated solutions were measured with a Synergy™ HTX Multi-Mode Microplate Reader ($\lambda$ex/em=360/460). In order to calculate the production rate of this fluorescent product, calibration curves using 7-hC (Sigma Aldrich, USA) were prepared.

For certain polymer solutions, interferences may be found between the solution and the reactants, invalidating the measure. In such cases, another method was used to determine the concentration of $H_2O_2$, $NO_2^-$ and $NO_2^-$ in the polymer solutions after plasma treatment: QUANTOFIX® test strips, which were analyzed by means of a reflexion photometer (QUANTOFIX® Relax, of Macherey Nagel). The strips consist of plastic strips to which test paper has been sealed. Nitrite strips are also based in Griess reagent. Peroxide strips also use a redox reaction. The range of detection of the test strips used for $H_2O_2$, $NO_3^-$ and $NO_2^-$ were 1-100 mg/L, 10-500 mg/L and 1-80 mg/L, respectively. The plasma-treated polymer solutions were diluted, if necessary, to be within the measuring range.

To test if the values for RONS concentrations obtained with the two methods disclosed above were equivalent, different solutions were tested with both methods.

Solutions of known concentrations were prepared (100, 50, 25 y 12.5 mg/L for hydrogen peroxide and 8.28, 4.14, 2.07, 1.035 mg/L for nitrites), and the concentration of hydrogen peroxide was measured with both the AR/HRP method and the strips method, while the concentration of $NO_2^-$ was measures with both the Griess reagent method and the strips method.

The four different dilutions of 30% $H_2O_2$ were prepared either in water or in a 0.5% wt alginate water solution, and $H_2O_2$ concentration was tested with both methods. Three replicates were tested for each point. As the following table shows, both methods give equivalent results:

| $H_2O_2$ detection from 30% $H_2O_2$ solution | | | |
| DI water | | 0.5% alginate | |
|---|---|---|---|
| AR/HRP reagent method | Strips method | AR/HRP reagent method | Strips method |
| 100.0 ± 2.26 | 98.0 ± 19.6 | 100.0 ± 5.38 | 101.3 ± 20.3 |
| 50.0 ± 1.99 | 47.3 ± 9.5 | 50.0 ± 1.18 | 52.0 ± 10.4 |
| 25.0 ± 0.52 | 23.3 ± 4.7 | 25.0 ± 0.68 | 25.7 ± 5.1 |
| 12.5 ± 0.16 | 12.7 ± 2.5 | 12.5 ± 4.42 | 12.3 ± 3.5 |
| 0 | Below minimum detection | 0 | Below minimum detection |

The four different dilutions of $NaNO_3$ were prepared either in water or in a 0.5% wt alginate water solution, and $NO_2^-$ concentration was tested with both methods. Three replicates were tested for each point. As the following table shows, both methods give equivalent results:

| $NO_2^-$ detection from dilutions of $NaNO_3$ powder (mg/L) | | | |
| DI water | | 0.5% alginate | |
|---|---|---|---|
| Griess reagent method | Strips method | Griess reagent method | Strips method |
| 8.28 ± 0.17 | 8.07 ± 1.61 | 8.28 ± 0.80 | 7.83 ± 1.57 |
| 4.14 ± 0.02 | 3.97 ± 0.79 | 4.14 ± 0.75 | 4.13 ± 0.83 |
| 2.07 ± 0.08 | 2.13 ± 0.43 | 2.07 ± 0.20 | 2.00 ± 0.40 |
| 1.04 ± 0.02 | 1.07 ± 0.21 | 1.04 ± 0.08 | 0.97 ± 0.19 |
| 0 | Below minimum detection | 0 | Below minimum detection |

Therefore, for the present invention, the RONS concentration is determined either using the AR/HRP reagent method and the Griess reagent method, or the strips method.

pH Monitoring.

The polymeric solution was placed in 24 well-plates and treated using kINPen or APPJ (10 mm, 1 L/min). pH was measured by using a PC80 Multiparameter instrument (XS Instruments, Italy) with a Crison 50 14 electrode (Crison, Spain).

SEM.

The compositions were freeze-dried and were C-coated using an EMITECH K950X Turbo Evaporator (Quorum Technologies Ltd., UK). All samples were imaged in a Phenom XL SEM (Phenom-World B.V., The Netherlands) under high vacuum at 5 kV and a 5 mm working distance.

Release of RONS.

200 µL of the polymeric solution in 96-well plate were treated by kINPen for 90 s, 10 mm and 1 L/min and APPJ for 15 min, 10 mm and 1 L/min.

After plasma-treatment, the polymeric solution was transferred to CORNING Transwell polyester membrane cell culture insert (Sigma-Aldrich), with a 6.5 mm diameter and a 0.4 µm pore size and placed in suspension in 1 mL volume of cell culture media in 24-well plates. For the monitoring of the release kinetics of RONS from the hydrogels 100 µL of the cell culture medium used as release media were withdrawn at determined time points for subsequent quantification of $NO_2^-$ and $H_2O_2$. 100 µL of fresh medium was replaced after each sample collection. Final volumes of release media have been measured at the end of release experiment to take into account the volume correction in the concentration calculations of $NO_2^-$ and $H_2O_2$. $NO_2^-$ and $H_2O_2$ were quantified as described in the previous section.

In Vitro Cell Experiments.

Cell Culture.

Sarcoma Osteogenic (SaOS-2) were used to study the cytotoxicity of the hydrogels and the compositions. The cell culture medium consisted of McCoy's 5A with 10% FBS and 1% P/S. Cells were grown in 75 cm² cell culture flasks at 37° C. in a 5% $CO_2$ incubator and upon reaching 80% confluence. SaOS-2 were detached from the flask using trypsin (Invitrogen, Thermofisher) and 10000 cells/well were seeded into 24-well plates with 1 mL volume of culture medium. After 6 h-adhesion, plasma-treated sterile polymer solutions, previously prepared in sterile conditions, were introduced into a CORNING Transwell polyester membrane cell culture insert and placed in suspension in the well, to evaluate the effect of kINPen and APPJ plasma treatment of the polymeric solution on the SaOs-2 cell viability. As positive control, the same number of cells was placed without adding polymeric solution or composition. The cells were grown at 37° C. in a 5 $CO_2$ incubator for another 72 h.

Bone marrow-derived Mesenchymal Stem Cells (hMSC) were used to evaluate the selectivity of the cytotoxicity of plasma-treated hydrogels between cancer and healthy cell lines. Cell culture medium of hMSC consisted of AdvD-MEM supplemented with 10% FBS and 1% P/S. Seeding, cell density and experimental design of hMSC were reproduced in the exact same conditions such as presented above with SaOS-2. hMSC cell viability was evaluated at 72 hours for cells in presence of untreated polymer solution (UT), and plasma-treated polymer solution at different treatment times.

Cell viability at 24 and 72 hours was evaluated with WST-1 reagent following supplier's protocol. Absorbance was measured at $\lambda_{abs}$=440 nm using a Synergy HTX Hybrid Multi Mode Microplate Reader (BioTek Instruments, Inc., USA). Normalization of the absorbance values was made with respect to cells only to determine the effects of untreated and plasma-treated Gel/Alg polymer solution on SaOS-2 cell viability.

Cell Viability.

Influence of plasma-treated polymeric solutions on SaOs-2 or hMSCs cell viability was evaluated for kINPen and APPJ (10 mm, 1 L/min) for 90 and 180 s of plasma treatments. Plasma-treated polymeric solutions were also studied for 180 s APPJ and kINPen plasma treatment. Cell viability was evaluated at 0, 24 and 72 hours. Cell culture media was replaced by preparation consisting of 250 μL of Cell Proliferation Reagent WST-1 in Mc Coy's 5A culture medium (1:10) and incubated for 1 hour at 37° C. Afterward, 100 μL of the supernatant were transferred to another well for absorbance measurement at 440 nm. To evaluate the effects untreated and plasma-treated polymer solutions on SaOs-2 cell viability, normalization of the values was made with respect to the well containing cells only.

Range of Concentrations of Reactive Species Generated in the Polymer Solution

The concentrations of reactive species generated by atmospheric pressure plasma treatment in 200 μL of polymer solution (gelatin/alginate as in Example 1) and in 1 mL of polymer solution, at different treatment times are shown below.

| kINPen | Detection method: Strips | | |
|---|---|---|---|
| | 200 μL | | |
| Treat. time (s) | $H_2O_2$ (mg/L) | $NO_2^-$ (mg/L) | $NO_3^-$ (mg/L) |
| 0 | 0 | 0 | 0 |
| 15 | 1.9 ± 0.4 | 1.3 ± 0.3 | <10 |
| 30 | 2.4 ± 0.5 | 2.6 ± 0.5 | 19 ± 3.8 |
| 45 | 4.5 ± 0.9 | 4.0 ± 0.8 | 25 ± 5.0 |
| 60 | 5.3 ± 1.1 | 4.3 ± 0.9 | 27 ± 5.4 |
| 90 | 7.7 ± 1.5 | 6.7 ± 1.3 | 44 ± 8.8 |
| 180 EXAMPLE 1) | 16.7 ± 3.3 | 17.0 ± 3.4 | 124 ± 24.8 |
| 300 (EXAMPLE 2) | 31.5 ± 6.3 | 22.0 ± 4.4 | 190 ± 38.0 |
| | 1 mL | | |
| t (s) | $H_2O_2$ (mg/L) | $NO_2^-$ (mg/L) | $NO_3^-$ (mg/L) |
| 0 | 0 | 0 | 0 |
| 180 | 15.8 ± 3.2 | 6.0 ± 1.2 | 48.7 ± 9.7 |
| 300 | 24.3 ± 4.9 | 9.1 ± 1.8 | 59.3 ± 11.9 |
| 600 | 62.0 ± 12.4 | 13.7 ± 2.7 | 103.7 ± 20.7 |
| 900 | 97.0 ± 19.4 | 21.3 ± 4.3 | 214.0 ± 42.8 |

| APPJ | Detection method: Strips | | |
|---|---|---|---|
| | 200 μL | | |
| Treat. time (s) | $H_2O_2$ (mg/L) | $NO_2^-$ (mg/L) | $NO_3^-$ (mg/L) |
| 0 | 0 | 0 | 0 |
| 15 | 2.7 ± 0.5 | 1.3 ± 0.3 | <10 |
| 30 | 4.8 ± 1.0 | 2.1 ± 0.4 | 24 ± 4.8 |
| 45 | 6.0 ± 1.2 | 3.2 ± 0.6 | 40 ± 8.0 |
| 60 | 6.6 ± 1.3 | 3.8 ± 0.8 | 55 ± 11.0 |
| 90 | 8.2 ± 1.6 | 5.0 ± 1.0 | 55 ± 11.0 |
| 180 | 13.6 ± 2.7 | 8.7 ± 1.7 | 49 ± 9.8 |
| 300 | 22.4 ± 4.5 | 11 ± 2.2 | 53 ± 10.6 |
| | 1 mL | | |
| t (s) | $H_2O_2$ (mg/L) | $NO_2^-$ (mg/L) | $NO_3^-$ (mg/L) |
| 0 | 0 | 0 | 0 |
| 180 | 7.1 ± 1.4 | 6.0 ± 1.2 | 53.0 ± 10.6 |
| 300 | 13.0 ± 2.6 | 11.0 ± 2.2 | 92.3 ± 18.5 |
| 600 | 21.7 ± 4.3 | 15.2 ± 3.0 | 134.0 ± 26.8 |
| 900 | 37.8 ± 7.6 | 18.5 ± 3.7 | 220.3 ± 44.0 |

| kINPen | Detection method: Strips | | | | | |
|---|---|---|---|---|---|---|
| 1 mL | 3 L/min | | | 1 L/min | | |
| Treat. time (min) | $H_2O_2$ (mg/L) | $NO_2^-$ (mg/L) | $NO_3^-$ (mg/L) | $H_2O_2$ (mg/L) | $NO_2^-$ (mg/L) | $NO_3^-$ (mg/L) |
| 0 | 0 | 0 | 0 | 0 | 0 | 0 |
| 10 | 25.2 ± 4.4 | 2.8 ± 1.4 | 27.9 ± 1.2 | 21.4 ± 6.5 | 15.2 ± 1.8 | 158.7 ± 18.0 |
| 15 | 54.1 ± 8.2 | 6.0 ± 0.5 | 71.9 ± 5.0 | 47.6 ± 6.1 | 23.5 ± 1.8 | 249.3 ± 22.3 |
| 20 | 83.3 ± 2.0 | 23.5 ± 3.7 | 288.3 ± 45.3 | 65.0 ± 11.2 | 62.1 ± 6.4 | 449.5 ± 23.6 |

US 12,691,145 B2

11

| | APPJ 1 mL Detection method: Strips Gas flow 1 L/min | | |
| Treat. | | | |
| time (min) | $H_2O_2$ (mg/L) | $NO_2^-$ (mg/L) | $NO_3^-$ (mg/L) |
| --- | --- | --- | --- |
| 0 | 0 | 0 | 0 |
| 5 | 16.3 ± 2.5 | 12.1 ± 3.5 | 115.6 ± 28.3 |
| 10 | 38.7 ± 10.1 | 28.7 ± 6.5 | 385.7 ± 32.3 |
| 15 | 58.3 ± 7.1 | 38.6 ± 2.9 | 409.7 ± 43.7 |
| 20 | 67.7 ± 7.1 | 41.3 ± 7.4 | 442.0 ± 32.2 |
| 30 | 138.7 ± 20.5 | 68.0 ± 8.7 | 624.0 ± 110.5 |

Example 0

Gelatin in powder was mixed with MilliQ water at 37° C. using magnetic stirring for 2 hours to obtain a 2% wt gelatin gel. 200 µL of this gelatine solution was treated with two types of atmospheric pressure plasma jet: i) kINPen IND® (Neoplas, Germany) operating with Argon, 1 L/min gas flow and 10 mm distance and ii) APPJ (a home-made atmospheric pressure plasma jet) operating with helium, 1 L/min gas flow and 10 mm distance. The reactive species generated after different plasma treatment times were quantified. Said plasma-treated gelatin solution was used in cell viability assays in both an osteosarcoma cell line (SaOS-2).

| | kINPen (200 µL, 1 L/min) | | APPJ (200 µL, 1 L/min) | |
| Treat. | | | | |
| time (s) | $H_2O_2$ (mg/L) | $NO_2^-$ (mg/L) | $H_2O_2$ (mg/L) | $NO_2^-$ (mg/L) |
| --- | --- | --- | --- | --- |
| 0 | 0 | 0 | 0 | 0 |
| 15 | 12.0 ± 6.3 | 3.8 ± 0.7 | 5.1 ± 1.2 | 1.0 ± 0.1 |
| 30 | 12.7 ± 2.7 | 7.2 ± 1.1 | 6.3 ± 0.9 | 1.6 ± 0.3 |
| 45 | 16.0 ± 4.9 | 9.6 ± 0.6 | 7.7 ± 1.3 | 2.7 ± 0.1 |
| 60 | 23.4 ± 3.6 | 11.7 ± 1.6 | 9.9 ± 1.1 | 3.3 ± 0.2 |
| 90 | 25.2 ± 5.2 | 10.4 ± 2.0 | 13.2 ± 1.2 | 5.1 ± 0.2 |
| 120 | 33.5 ± 1.9 | 12.3 ± 1.3 | 18.2 ± 3.2 | 6.0 ± 0.6 |
| 180 | 47.7 ± 3.9 | 19.1 ± 0.8 | 26.4 ± 3.9 | 7.2 ± 0.1 |
| 300 | 79.1 ± 5.2 | 27.0 ± 1.5 | 37.5 ± 1.1 | 7.6 ± 0.5 |

The concentrations of reactive species generated in the gelatin solutions upon plasma treatment are higher than those disclosed until now, and the gelatin hydrogels comprising said RONS concentrations display an enhanced cytotoxicity on osteosarcoma cell line SaOS-2.

| Plasma treatment conditions | Cell viability at 24 h (%) (200 µL, 1 L/min) | Cell viability at 72 h (%) (200 µL, 1 L/min) |
| --- | --- | --- |
| Cells only | 100 | 100 |
| Untreated | 101.74 ± 1.87 | 88.76 ± 10.98 |
| APPJ 30 s | 70.93 ± 7.72 | 71.35 ± 2.33 |
| APPJ 90 s | 48.84 ± 0.65 | 23.88 ± 0.32 |
| APPJ 180 s | 46.51 ± 2.61 | 22.75 ± 0.33 |
| kINPen 30 s | 57.56 ± 0.31 | 44.94 ± 3.30 |
| kINPen 90 s | 36.63 ± 3.73 | 15.73 ± 2.07 |
| kINPen 180 s | 26.74 ± 4.24 | 12.36 ± 0.71 |

Example 1

A 50/50 blend of 0.5 weight % alginate and 2 weight % gelatin solutions were prepared (final concentration of 0.25% wt alginate and 1 wt gelatin).

The mixture of alginate/gelatin was prepared is by vortexing in a ratio 1:1, 2% wt gelatin with 0.5% wt alginate for 2 minutes. Gelatin in powder is mixed with MilliQ water at 37° C. using magnetic stirring for 2 hours to obtain a 2% wt gelatin gel. 0.5% alginate was prepared by mixing alginate powder with MilliQ water using a SpeedMixer™ DAC 150.1 FVZ-K (SpeedMixer™, Germany) at 3500 r.p.m. for 15 min.

The 0.25% wt alginate and 1 wt gelatin aqueous mixture was treated with an atmospheric pressure plasma jet kINPen IND® (Neoplas, Germany) operating with Argon to generate plasma. Treatment conditions: 1 L/min gas flow, 10 mm nozzle distance, and 180 seconds treatment. Treatment performed in 200 µL of mixture in a 96-well plate.

Said plasma-treated mixture produced the following concentrations of reactive species in the material:

| | $H_2O_2$ (mg/L) | $NO_2^-$ (mg/L) | $NO_3^-$ (mg/L) |
| --- | --- | --- | --- |
| Water | 10.3 | 2.6 | — |
| Example 1 | 16.7 | 17.0 | 124.0 |

All values have a ±20% variability due to the measuring method.

As shown in the table, the values of reactive species obtained in the composition of example 1 are several-fold higher than those generated in water.

Said plasma-treated mixture was used in cell viability assays in both an osteosarcoma cell line (SaOS-2) and in healthy cells (human bone marrow mesenchymal stem cells or hBM-MSC):

| Example 1 | Cell viability at 72 h (%) |
| --- | --- |
| SaOS-2 | 40.94 ± 3.44 |
| hBM-MSC | 90.57 ± 8.19 |

The composition of example 1 shows selectivity of the plasma-treated polymer solution on cancer cell line, allowing the survival of healthy cells (hBM-MSC) after 72 hours.

Example 2

An aqueous mixture comprising 0.25% wt alginate and 1 wt gelatin was treated with an atmospheric pressure plasma jet kINPen IND® (Neoplas, Germany) operating with Argon to generate plasma. Treatment conditions: 1 L/min gas flow, 10 mm nozzle distance, and 300 seconds treatment. Treatment performed in 200 µL of mixture in a 96-well plate. Said plasma-treated mixture produced the following concentrations of reactive species in the material, which are much higher than in water:

| | $H_2O_2$ (mg/L) | $NO_2^-$ (mg/L) | $NO_3^-$ (mg/L) |
| --- | --- | --- | --- |
| Water | 29.3 | 2.7 | — |
| Example 2 | 31.5 | 22.0 | 190.0 |

All values have a ±20% variability due to the measuring method.

Said plasma-treated mixture was used in cell viability assays in both an osteosarcoma cell line (SaOS-2) and in control cells (human bone marrow mesenchymal stem cells or hBM-MSC):

| Example 2 | Cell viability at 72 h (%) |
|---|---|
| SaOS-2 | 6.60 ± 0.27 |
| hBM-MSC | 94.38 ± 2.80 |

The composition of example 2 also shows selectivity of the plasma-treated polymer solution on cancer cell line, allowing the survival of healthy cells (hBM-MSC) after 72 hours.

Example 3

An aqueous mixture comprising 0.25% wt alginate and 1% wt gelatin was treated with an atmospheric pressure plasma jet operating with Helium to generate plasma. Treatment conditions: 1 L/min gas flow, 10 mm nozzle distance, and 180 seconds treatment. Treatment performed on 200 μL of mixture in a 96-well plate.

The said plasma-treated mixture produced the following concentrations of reactive species in the material, which are much higher than those produced in water:

| | $H_2O_2$ (mg/L) | $NO_2^-$ (mg/L) | $NO_3^-$ (mg/L) |
|---|---|---|---|
| Water | 9.2 | 1.7 | — |
| Example 3 | 13.6 | 8.7 | 49.0 |

All values have a ±20% variability due to the measuring method.

Said plasma-treated mixture was used in cell viability assays in both an osteosarcoma cell line (SaOS-2) and in control cells (human bone marrow mesenchymal stem cells or hBM-MSC):

| Example 3 | Cell viability at 72 h (%) |
|---|---|
| SaOS-2 | 50.08 ± 1.99 |
| hBM-MSC | 95.03 ± 1.44 |

The composition of Example 3 also shows selectivity of the plasma-treated polymer solution on cancer cell line, allowing the survival of healthy cells (hBM-MSC) after 72 hours.

Example 4

An aqueous mixture comprising 0.25% wt alginate and 1% wt gelatin was treated with an atmospheric pressure plasma jet operating with Helium to generate plasma. Treatment conditions: 1 L/min gas flow, 10 mm nozzle distance, and 300 seconds treatment. Treatment performed on 200 μL of mixture in a 96-well plate.

Said plasma-treated mixture produced the following concentrations of reactive species in the material, which are much higher than those produced in water:

| | $H_2O_2$ (mg/L) | $NO_2^-$ (mg/L) | $NO_3^-$ (mg/L) |
|---|---|---|---|
| Water | 16.4 | 2.7 | — |
| Example 4 | 22.4 | 11.0 | 53.0 |

All values have a ±20% variability due to the measuring method.

Said plasma-treated mixture was used in cell viability assays in both an osteosarcoma cell line (SaOS-2) and in control cells (human bone marrow mesenchymal stem cells or hBM-MSC):

| Example 4 | Cell viability at 72 h (%) |
|---|---|
| SaOS-2 | 11.24 ± 1.69 |
| hBM-MSC | 94.79 ± 2.01 |

Example 5

The compositions of Examples 1 to 4 were prepared comprising 5% wt of calcium deficient hydroxyapatite microspheres (MS), which were added and mixed in the vortex for 2 min. The diameter of the microspheres was 100 μm<Ø<150 μm. The compositions were freeze-dried to perform scanning electron microscopy. Example 5 corresponds to composition of Example 1 (5-min kINPen treatment of the alginate/gelatin blend)+5% wt of calcium deficient hydroxyapatite microspheres. The amount of reactive species in the composition is proportional to the percent of polymer solution of Examples 1 to 4. The amount of RONS was not affected by the addition of the bioceramic material.

The concentration of reactive species generated by plasma in the polymer solution and in the composition after adding the bioceramic material is equivalent, as can be seen below:

| Example | $[H_2O_2]$ (mg/L) | $[NO_2^-]$ (mg/L) | $[NO_3^-]$ (mg/L) |
|---|---|---|---|
| 1 | 78.0 ± 15.6 | 20.0 ± 4.0 | 297.0 ± 59.4 |
| 5 (Example 1 + 5% microspheres) | 84.7 ± 16.9 | 21.5 ± 4.3 | 270.0 ± 54.0 |

The species generated in the composition of Example 5 can be released to a surrounding media and preserved at least for 24 hours:

| | $H_2O_2$ concentration in 1 mL release media (mg/L) | | |
|---|---|---|---|
| Time (h) | Example 1 | Example 5 | Example 5 with DOX-loaded MS |
| 0 | 0 | 0 | 0 |
| 0.5 | 2.37 ± 0.15 | 3.11 ± 0.19 | 3.18 ± 0.11 |
| 1 | 2.55 ± 0.37 | 4.18 ± 0.39 | 2.57 ± 0.09 |
| 2 | 1.99 ± 0.34 | 3.50 ± 0.25 | 2.64 ± 0.09 |
| 4 | 2.08 ± 0.33 | 3.76 ± 0.39 | 3.06 ± 0.10 |
| 24 | 1.95 ± 0.23 | 3.06 ± 0.64 | 2.21 ± 0.08 |

| | $NO_2^-$ concentration in 1 mL release media (mg/L) | | |
|---|---|---|---|
| Time (h) | Example 1 | Example 5 | Example 5 with DOX-loaded MS |
| 0 | 0 | 0 | 0 |
| 0.5 | 0.25 ± 0.02 | 0.25 ± 0.03 | 0.25 ± 0.05 |
| 1 | 0.31 ± 0.02 | 0.36 ± 0.04 | 0.29 ± 0.06 |
| 2 | 0.38 ± 0.01 | 0.46 ± 0.01 | 0.35 ± 0.07 |
| 4 | 0.43 ± 0.02 | 0.51 ± 0.03 | 0.29 ± 0.06 |
| 24 | 0.54 ± 0.06 | 0.60 ± 0.04 | 0.32 ± 0.06 |

Said Example 5 was used in cell viability assays in osteosarcoma cell line (SaOS-2):

| | SaOS-2 cell viability at 24 h (%) | SaOS-2 cell viability at 72 h (%) |
|---|---|---|
| Untreated composition | 93.6 ± 6.8 | 96.7 ± 2.1 |
| Example 5 | 13.8 ± 1.3 | 7.5 ± 5.5 |

Example 6

Example 6 corresponds to the composition of Example 2 (5-min kINPen treatment of the alginate/gelatin blend)+5% wt of calcium deficient hydroxyapatite microspheres. The composition was freeze-dried and photographed by SEM (FIG. 1). The amount of reactive species in the composition was proportional to the percent of polymer solution of examples 1 to 4. The amount of RONS was not affected by the addition of the bioceramic material.

The concentration of reactive species generated by plasma in the polymer solution and in the composition after adding the bioceramic material is equivalent, as can be seen below:

| Example | $[H_2O_2]$ (mg/L) | $[NO_2^-]$ (mg/L) | $[NO_3^-]$ (mg/L) |
|---|---|---|---|
| 2 | 118.3 ± 23.7 | 28.5 ± 5.7 | 346.0 ± 69.2 |
| 6 (Example 2 + 5% microspheres) | 96.7 ± 19.3 | 30.0 ± 6.0 | 364.0 ± 72.8 |

Said Example 6 was used in cell viability assays in osteosarcoma cell line (SaOS-2):

| | SaOS-2 cell viability at 24 h (%) | SaOS-2 cell viability at 72 h (%) |
|---|---|---|
| Untreated material | 93.6 ± 6.8 | 96.7 ± 2.1 |
| Example 6 | 7.4 ± 0.1 | 2.6 ± 0.1 |

Example 7

The compositions of Examples 1 to 4 were prepared comprising 5% wt of hydroxyapatite nanoparticles. These compositions were tested for injectability and it was found that all were fully injectable.

Example 8

Figure 2:
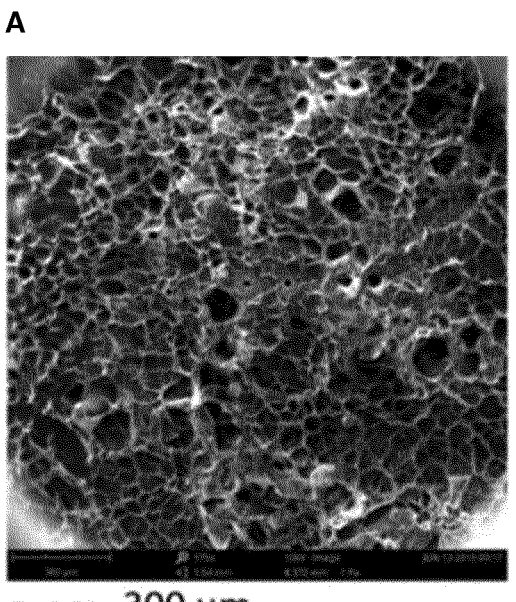
FIG. 2: SEM image of the freeze-dried composition sample of example 8 without RONS (A) and with RONS (B).
Figure 2:
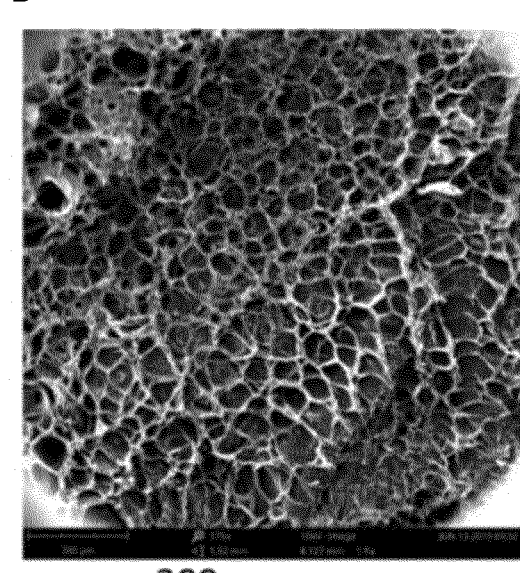

A composition comprising a polymeric aqueous solution containing gelatin 6.5% wt, fibrinogen 10 mg/mL and aprotinin 1 μg/mL and 0.5% wt hydroxyapatite nanoparticles was prepared. Plasma treatment conditions: 1 L/min gas flow, 10 mm nozzle distance, and 5 min treatment, performed on 1000 μL of the composition (FIG. 2). Injectability was always good, with slightly higher values for RONS comprising compositions, but still keeping proper injectability for use.

Example 9

Figure 3:
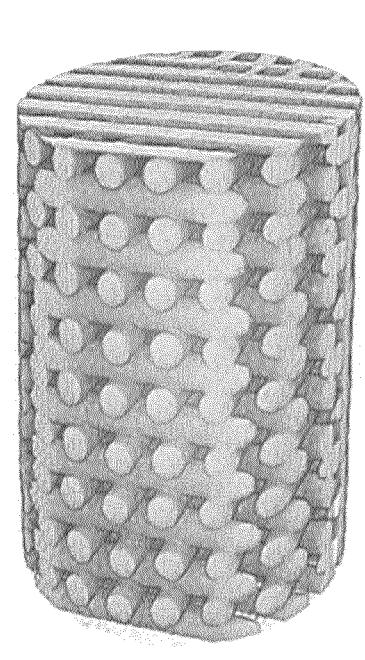
FIG. 3: Example of reconstruction of the 3D scaffold (A), and SEM image of the freeze-dried composition of Example 9 (B).
Figure 3:
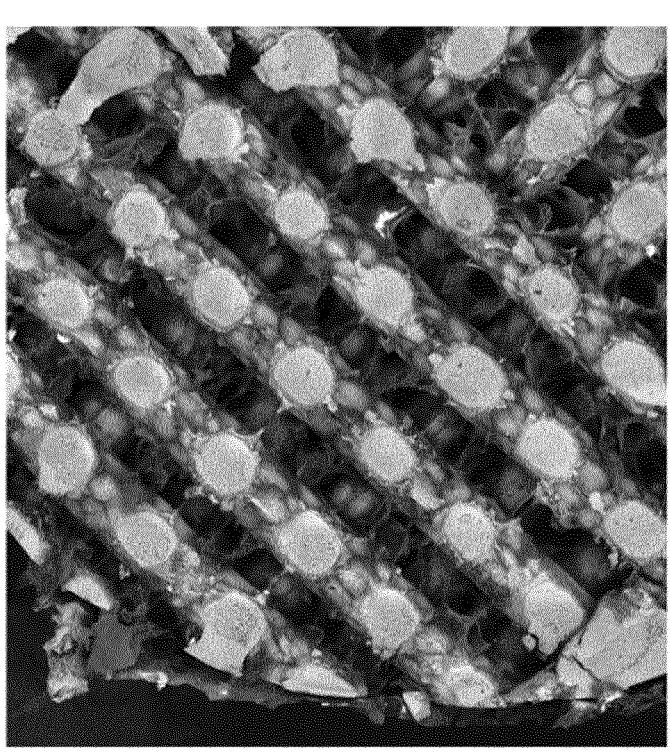

A composition comprising a polymeric aqueous solution containing 0.25% wt alginate and 1% wt gelatin was treated with an atmospheric pressure plasma jet kINPen IND operating with Argon to generate plasma. Treatment conditions: 1 L/min gas flow, 10 mm nozzle distance, and 180 seconds treatment. Treatment performed in 200 μL of mixture in a 96-well plate, and then loaded to a calcium phosphate scaffold, to obtain a composition with a final 55% wt of calcium-deficient hydroxyapatite, in respect of the total weight of the composition. In this example, the polymer solution is embedded within the 3D-printed scaffold (FIG. 3). This composition was implanted into a 5 mm condyle defect of healthy New Zealand rabbits. The animals were euthanized two months after the surgical procedure and bone regeneration was assessed by micro-computed tomography and SEM.

Figure 4:
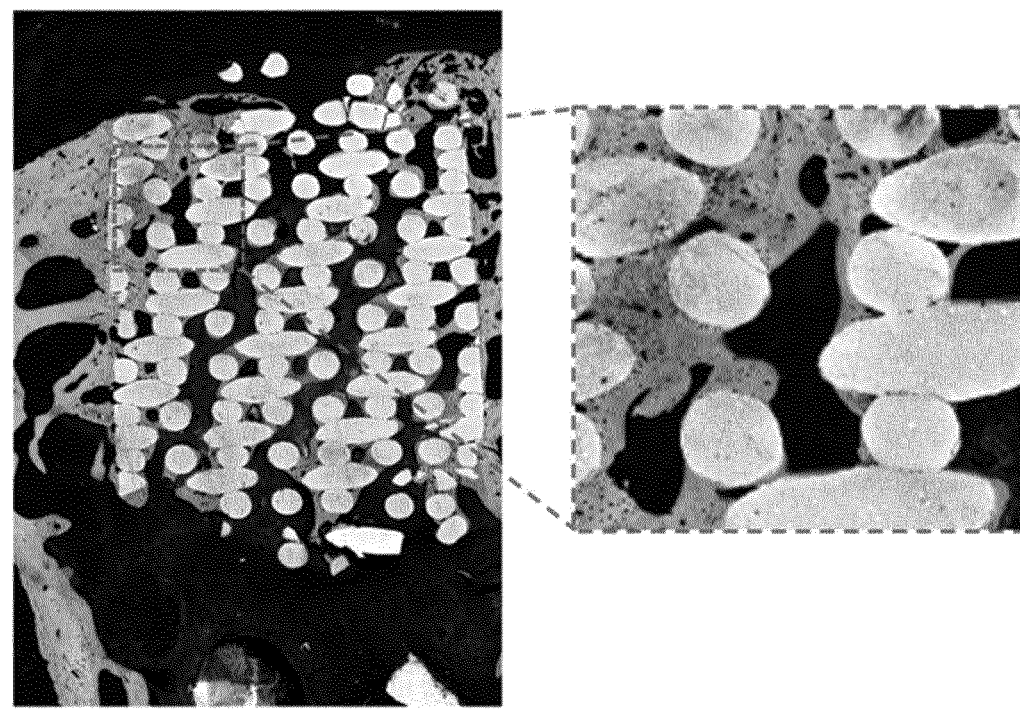
FIG. 4: SEM image showing bone ingrowth within the composition of Example 9.

The composition of Example 9 (Scaffold+hydrogel containing plasma-generated RONS) demonstrated in vivo safety, allowing equivalent bone regeneration than the same composition without RONS (Scaffold+hydrogel without plasmas treatment) (FIG. 4).

The amount of regenerated bone in the scaffolds was quantified from micro-computed tomography images. Considering that the degradation of the scaffold can be negligible, macropore volume corresponds to the sum of newly formed bone and void pixels. Therefore, the average bone regeneration was calculated as BV/MV, being BV the volume of the newly formed bone and MV the macropore volume. The average bone regeneration was calculated and reported as mean±standard deviation (SD).

| Kind of sample | Bone regeneration (%) |
|---|---|
| Example 9 without plasma treatment | 39.97 ± 5.98 |
| Example 9 | 40.10 ± 3.36 |

The percentage of bone regeneration being equivalent in both samples confirms the safety of the plasma-treated composition. The composition of the Example 9 does not hinder the proliferation of healthy bone cells of the rabbit and allows similar bone ingrowth to bioceramic-based bone grafts. Therefore, the composition of the Example 9 can be used to treat bone cancer since it does not damage healthy cells and allows bone regeneration.

Example 10

Figure 5:
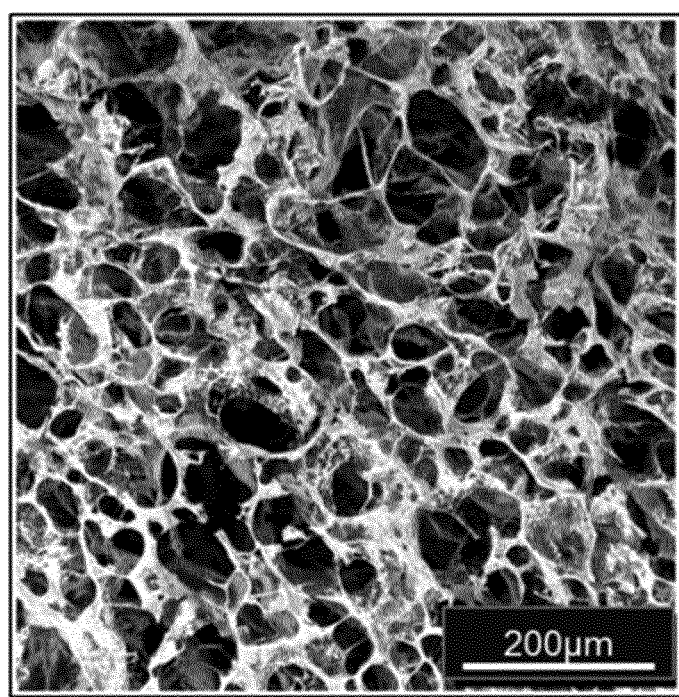
FIG. 5: SEM picture of freeze-dried composition of Example 10.

A composition comprising a 4 mg/mL collagen type I aqueous solution and 58% wt dry of hydroxyapatite nanoparticles was prepared. The composition was freeze-dried for SEM analysis (FIG. 5).

Example 11

Figure 6:
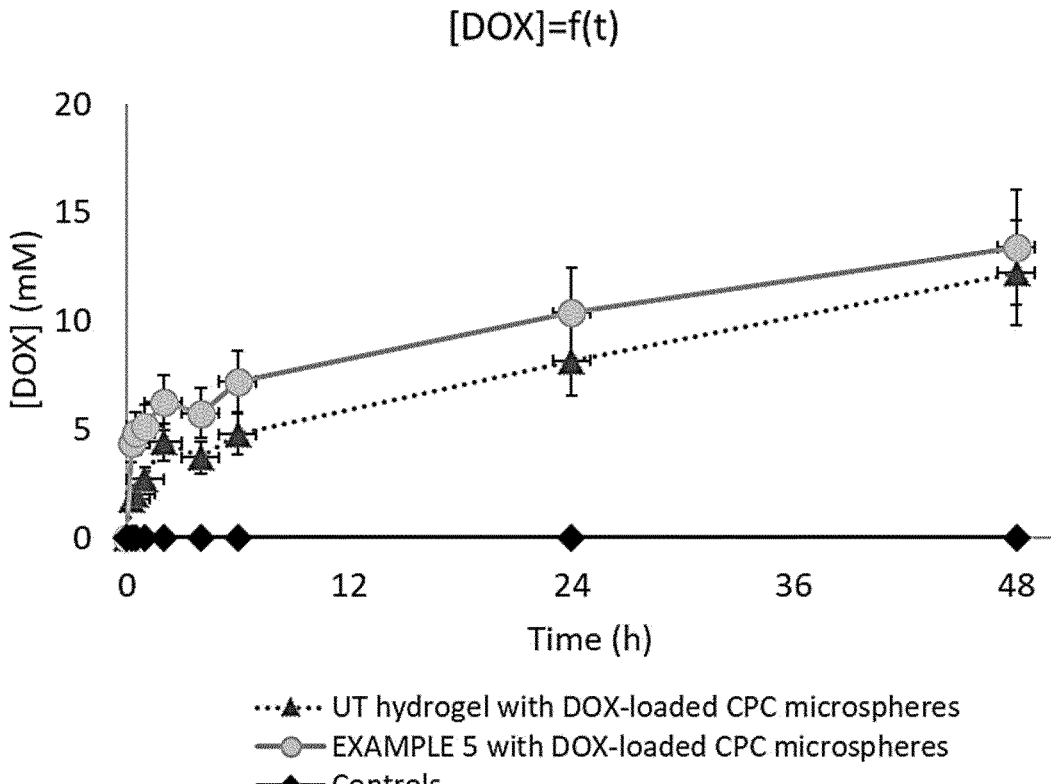
FIG. 6: Release of doxorubicin (DOX) from the composition of Example 11 (where calcium phosphate cement (CPC) microspheres have been previously loaded with doxorubicin), and untreated-hydrogel with DOX-loaded CPC microspheres to MilliQ water release media. 200 μL of composition were put in contact to 1 mL of MilliQ water.

The composition such as that of Example 5 was prepared where the calcium phosphate (CPC) microspheres had been previously loaded with doxorubicin. As control, untreated-hydrogel with DOX-loaded CPC microspheres were assayed for the release of RONS. 200 μL of composition were put in contact to 1 mL of MilliQ water. FIG. 6 shows that the loading of reactive species inside the hydrogel, does not affect the release of the active principle (doxorubicin) from the biomaterial.

Example 12

A composition comprising a 2% wt methacrylated-gelatin (GelMA) solution was treated with plasma. It was observed that higher amounts of RONS were obtained in said composition than a phosphate buffer saline (PBS) using the same treatment.

| PBS | | |
|---|---|---|
| t (min) | $H_2O_2$ (mg/L) | $NO_2^-$ (mg/L) |
| 0 | 0.00 | 0.00 |
| 2 | 3.96 ± 0.33 | 2.04 ± 0.46 |
| 4 | 7.33 ± 0.60 | 3.85 ± 1.12 |
| 6 | 10.76 ± 0.49 | 6.12 ± 1.54 |
| 8 | 13.99 ± 3.15 | 8.36 ± 1.93 |
| 10 | 16.94 ± 0.54 | 9.08 ± 1.82 |

| 2% GelMA | | |
|---|---|---|
| t (min) | $H_2O_2$ (mg/L) | $NO_2^-$ (mg/L) |
| 0 | 0.00 | 0.00 |
| 2 | 3.63 ± 1.85 | 7.83 ± 3.82 |
| 4 | 5.71 ± 2.54 | 12.34 ± 1.51 |
| 6 | 9.72 ± 4.13 | 18.52 ± 1.22 |
| 8 | 15.62 ± 2.20 | 20.82 ± 3.50 |
| 10 | 23.68 ± 4.88 | 24.60 ± 3.39 |

Example 13

A composition comprising a polymeric solution containing methylcellulose 1% wt solubilized in a phosphate solution containing 200 mM of $Na_2HPO_4$ was treated with an atmospheric pressure plasma jet kINPen IND® (Neoplas, Germany) operating with Argon to generate plasma. Treatment conditions: 1 L/min gas flow, 10 mm nozzle distance. The treatment was performed in 1000 μL of solution in a 24-well plate. Said plasma-treated solution produced the following concentrations of RONS in the material:

| treatment time (s) | $H_2O_2$ (mg/L) | $NO_2^-$ (mg/L) |
|---|---|---|
| 0 | 0 | 0 |
| 30 | 1.31 ± 0.23 | 0.50 ± 0.06 |
| 60 | 1.76 ± 0.39 | 0.87 ± 0.14 |
| 120 | 4.09 ± 0.55 | 1.53 ± 0.29 |
| 180 | 5.66 ± 0.66 | 2.09 ± 0.31 |
| 300 | 11.06 ± 0.40 | 2.66 ± 0.22 |

Moreover, the production rate of hydroxyl radical (OH*) during plasma treatment was estimated using the chemical probe coumarin. Said plasma-treated solution produced the following concentrations of 7-hydroxcoumarin (7-hC) in the material, which leads to a formation rate of 0.0002 μM/s:

| treatment time (s) | 7-hC (μM) |
|---|---|
| 0 | 0 |
| 60 | 0.0146 |

-continued

| treatment time (s) | 7-hC (μM) |
|---|---|
| 180 | 0.0261 |
| 300 | 0.0563 |

Example 14

A composition comprising an alginate/gelatin blend such as the one described in Example 2, treated during 5 minutes with kINPen treatment was mixed with 1% wt of calcium deficient hydroxyapatite microspheres, which had been loaded with doxorubicin (1%). The amount of reactive species in the composition is that of examples 2 and 6, as the amount of RONS was not affected by the addition of the bioceramic material. The microspheres had a size of 100 to 150 microns diameter (from 0% to 5% drug load). The plasma treatment was performed in 1 ml in 24-well plates with kINPen; Argon; 10 mm; 1 L/min; 5 min.

A synergic effect can be observed in the cancer cell cytotoxicity with the combination of doxorubicin contained in the microspheres and RONS from the alginate/gelatin hydrogel. In this sense, the amount of doxorubicin can be reduced 4 times when RONS are delivered simultaneously by the hydrogel. The following table shows the MG63 cells viability in the presence of the hydroxyapatite microspheres (MS) loaded with 1, 2, 3, 4 or 5% doxorubicin and in the presence of the hydroxyapatite microspheres loaded with 1% doxorubicin in combination with untreated (UT) or with plasma treated (PT) alginate/gelatin hydrogels (HG):

| | | Microspheres alone | | | | | Composite | |
|---|---|---|---|---|---|---|---|---|
| | Cells only | 1% MS | 2% MS | 3% MS | 4% MS | 5% MS | UT HG 1% MS | PT HG 1% MS |
| 24 h | 100 ± 0 | 83.5 ± 0.8 | 72.4 ± 2.4 | 65.5 ± 3.8 | 55.4 ± 0.1 | 55.1 ± 1.3 | 88.6 ± 1.4 | 72.4 ± 1.6 |
| 72 h | 100 ± 0 | 76.0 ± 9.1 | 40.2 ± 10.5 | 29.0 ± 2.1 | 26.1 ± 1.5 | 25.4 ± 0.8 | 80.0 ± 1.5 | 26.9 ± 0.5 |

20.000 MG63 cells were plated per well in DMEM cell culture medium in 24-well plates and left for 24-hour adhesion. Prior to the material addition, the cell culture medium was changed (DMEM-Pyr). 2004 of material was added 2 hours after. The cells were kept in an incubator at 37° C.; 95% hum.; 5% $CO_2$.

The invention claimed is:

1. A composition comprising a polymer aqueous solution, a bioceramic material comprising calcium, and reactive oxygen and nitrogen species (RONS), wherein the RONS comprises between 0.68 and 200.00 mg/L $H_2O_2$ and between 13.80 and 36.80 mg/L $NO_2^-$.

2. The composition according to claim 1, wherein the RONS comprises between 12.00 and 150.00 mg/L $H_2O_2$.

3. The composition according to claim 1, wherein the polymer is selected from gelatin and its derivatives, fibrin, fibronectin, collagen, and collagen derivatives, alginate, agarose, cellulose, modified cellulose, xanthan gum, polyethylene glycol, hyaluronic acid, chitosan, polylactide-co-glycolide, polyhydroxyalcanoates and mixtures thereof.

4. The composition according to claim 1, wherein the composition comprises between 0.15 and 50.00 weight % of polymer in respect of the total weight of the composition.

5. The composition according to claim 1, wherein the bioceramic material comprising calcium preferably comprises calcium phosphate, and is selected from tetra-calcium phosphate, dicalcium phosphate anhydrous, dicalcium phosphate dihydrate, alpha-tricalcium phosphate, beta-tricalcium phosphate, monocalcium phosphate monohydrate, hydroxyapatite, calcium deficient hydroxyapatite, fluorapatite, amorphous calcium phosphate, calcium-sodium and potassium-phosphate, calcium- and sodium-phosphate, calcium- and potassium-phosphate, calcium pyrophosphate, calcium carbonate, calcium sulphate, calcium sulphate hemihydrate, calcium oxide and calcium hydroxide, and mixtures thereof.

6. The composition according to claim 1, wherein the bioceramic material is hydroxyapatite, brushite, tricalcium phosphate or mixtures thereof.

7. The composition according to claim 1, wherein the bioceramic material is in form of nanoparticles, microspheres, microparticles, foams or scaffolds, or mixtures thereof.

8. The composition according to claim 1, wherein the composition comprises between 0.5 and 99.5 weight % of bioceramic materials in respect of the total weight of the composition.

9. The composition according to claim 1, wherein the pH of the composition is between 5.0 and 8.0, preferably between 6.0 and 7.5, measured according to ASTM E70.

10. The composition according to claim 1, further comprising an active pharmaceutical ingredient.

11. The composition according to claim 10, wherein the active pharmaceutical ingredient is a chemotherapeutic drug or a co-adjuvant in the cancer therapy.

12. The composition according to claim 1, wherein the reactive oxygen and nitrogen species are generated by means of treating either the polymer aqueous solution or the polymer aqueous solution and the bioceramic material comprising calcium, with cold atmospheric plasma.

13. The composition according to claim 1, wherein the gelatin and its derivative is methacrylated gelatin.

14. The composition according to claim 1, wherein the modified cellulose is selected from hydroxypropyl cellulose, methylcellulose, carboxymethylcellulose or hydroxyethyl cellulose.

15. The composition according to claim 1, wherein the polymer is selected from gelatin, alginate, collagen and mixtures thereof.

16. The composition according to claim 1, wherein the RONS comprises between 13.60 and 150.00 mg/L $H_2O_2$ and between 18.40 and 36.80 mg/L $NO_2^-$.

17. A method for treating bone cancer and/or bone tissue regeneration, the method comprising the step of:

administering a composition to a patient, the composition comprising a polymer aqueous solution, a bioceramic material comprising calcium, and reactive oxygen and nitrogen species (RONS), wherein the RONS comprises between 0.68 and 200.00 mg/L $H_2O_2$ and between 13.80 and 36.80 mg/L $NO_2^-$, as a treatment method for bone cancer or as a treatment to induce bone tissue regeneration.

* * * * *